United States Patent
Webster (10) Patent No.: US 6,184,264 B1
(45) Date of Patent: Feb. 6, 2001

(54) ADHESIVES

(75) Inventor: Iain Webster, Osbaldwick (GB)

(73) Assignee: Smith & Nephew plc (GB)

( * ) Notice: Under 35 U.S.C. 154(b), the term of this patent shall be extended for 0 days.

(21) Appl. No.: 09/011,557

(22) PCT Filed: Aug. 12, 1996

(86) PCT No.: PCT/GB96/01954

§ 371 Date: Mar. 26, 1998

§ 102(e) Date: Mar. 26, 1998

(87) PCT Pub. No.: WO97/06836

PCT Pub. Date: Feb. 27, 1997

(30) Foreign Application Priority Data

| Aug. 11, 1995 | (GB) | ................................................ 9516487 |
| Nov. 9, 1995 | (GB) | ................................................ 9522938 |
| Jul. 18, 1996 | (GB) | ................................................ 9615125 |
| Jul. 18, 1996 | (GB) | ................................................ 9615127 |

(51) Int. Cl.$^7$ ..................................................... C08F 2/46
(52) U.S. Cl. ............................. 522/182; 522/6; 522/120; 522/121; 522/904; 522/905; 427/516; 427/208.4; 428/41.7; 428/41.8; 428/42.3; 428/355 R; 156/272.2; 156/273.3; 156/275.5; 156/275.7
(58) Field of Search .................................... 522/120, 121, 522/182, 904, 905; 427/516, 208.4; 428/41.7, 41.8, 42.3, 355 R; 156/272.2, 275.5, 273.3, 275.7

(56) References Cited

U.S. PATENT DOCUMENTS

| 4,286,047 | * | 8/1981 | Bennett et al. ....................... 430/280 |
| 4,810,523 | * | 3/1989 | Williams et al. ...................... 427/36 |
| 4,847,137 | * | 7/1989 | Kellen et al. ......................... 428/195 |
| 5,032,637 | * | 7/1991 | Therrlault et al. .................... 524/375 |
| 5,110,388 | * | 5/1992 | Komiyama et al. .................. 156/229 |
| 5,187,007 | * | 2/1993 | Ebe et al. .............................. 428/434 |
| 5,255,979 | * | 10/1993 | Ferrari .................................. 374/158 |
| 5,281,473 | * | 1/1994 | Ishiwata et al. ...................... 428/345 |
| 5,525,422 | * | 6/1996 | Spies et al. ........................... 428/355 |
| 5,641,310 | * | 3/1997 | Delgado et al. .................. 428/316.6 |

FOREIGN PATENT DOCUMENTS

| 2070631 | * | 9/1981 | (GB) . |
| 88/01878 | * | 3/1988 | (WO) . |
| 96/29374 | * | 9/1996 | (WO) . |

* cited by examiner

Primary Examiner—James J. Seidleck
Assistant Examiner—Sanza McClendon
(74) Attorney, Agent, or Firm—Larson Taylor PLC (57) ABSTRACT

There are described novel adhesives, which are capable of being "switched" form a tack to a non-tacky state. Such switchable adhesives are especially advantageous when used in medical dressings, and therefore, novel medical dressings comprising a switchable adhesive layer, a removable light occlusive layer and an intermediate transparent or translucent layer are also described.

15 Claims, 1 Drawing Sheet

ADHESIVES

The present invention relates to adhesives, to methods for producing adhesives and to articles comprising adhesives. In particular this invention relates to 'switchable' adhesives, that is, adhesives which may be influenced to change from a tacky to a non-tacky state thereby reducing the peel strength of the adhesive.

Adhesive products such as adhesive surgical or medical dressings and bandages normally comprise a layer of a pressure sensitive adhesive. However, when conventional adhesive dressings and/or bandages are removed they often cause localised trauma to the patient.

There has therefore long been a desire to provide, for example, adhesive dressings which can exhibit a reduction in peel strength of the adhesive, and therefore cause less localised trauma, than conventional adhesives when the dressing is removed. Hereinafter, adhesives which can be changed from a tacky to a non-tacky state will be referred to as 'switchable adhesives'.

Switchable adhesives are known. For example, U.S. Pat. Nos. 5,032,637, 5,352,516, 4,331,576 and 5,182,323 describe adhesives which become less tacky, ie. are switchable, in contact with water. However, such adhesives are unsuitable, for example, if used on a wound dressing and the patients wound needs to be kept dry. UV switchable adhesives are described in U.S. Pat. Nos. 4,286,047, 4,968, 559 and 5,118,567 and Japanese Patent No.3043988. Such adhesives suffer from the disadvantage that they may require high doses of UV radiation or may need to be used in conjunction with photoinitiators which result in undesirable bi-products. Since it remains undesirable to expose patients to too much ultra violet radiation, there remains a need for a switchable adhesive which can undergo a reduction in peel strength at low dosages of UV radiation or more preferably by exposure to visible light irradiation and/or which removes or mitigates the need for the use of photoinitiators.

We have now surprisingly found an adhesive which is switchable when exposed to, inter alia, visible light, ie. is visible light switchable, or low dosages of UV light. Such visible light switchable or low dosage UV light switchable adhesives generally comprise an adhesive polymeric group with bound-in polymerisable or curable group.

Thus according to the invention we provide a switchable adhesive composition comprising an adhesive polymeric moiety and a plurality of bound-in curable moieties.

The bound-in curable moieties are preferably photocurable moieties. By the term curable moieties we mean moieties which are capable of undergoing a reaction, eg. photo curing to produce a polymer comprising the adhesive polymeric group, which polymer has greatly increased molecular weight. The preferred curable moieties are those which produce a polymer of increased molecular weight by way of cross-linking the adhesive polymeric moiety.

The bound-in curable moiety may be introduced into the adhesive polymeric moiety by forming a polymer comprising the adhesive polymeric moiety and the bound-in curable moiety, eg. the curable moiety is chemically bound to the adhesive polymeric moiety.

The adhesive polymeric moiety will generally comprise a polymeric 'backbone'. Any conventionally known adhesive polymers may be used provided that such polymers are, where desirable, reactable to produce adducts with curable moieties such that the curable moieties are bound-in.

Preferred adhesive polymeric moieties include polyurethanes, polyacrylates and free radical polymerisable vinyl moieties. Polyacrylates are especially preferred.

When the adhesive polymeric moiety comprises a polyurethane adhesive it may be a lightly cross-linked or linear polyurethane adhesive. When the adhesive polymeric moiety is a polyurethane the bound-in curable groups may form end groups on the polyurethane backbone, may be incorporated into the polymer backbone or may be pendant groups, eg. along the backbone.

Desirably the bound-in curable groups in the polyurethane adhesives are located at or close to free ends of the backbone and curing causes these ends to become linked together.

Particularly preferred adhesives are acrylates. By the term acrylate adhesives we include acrylates, methacrylates and acrylate copolymer adhesives. Indeed acrylate copolymer adhesives are especially preferred, eg. alkyl acrylate copolymers. The 'backbone' polymer may be a copolymer with one or more acrylates. Alternatively the 'backbone' polymer may be a copolymer with one or more acrylates and a free radical polymerisable vinyl moiety. Such vinyl moieties include compounds such as itaconic anhydride, maleic anhydride or vinyl azlactone or glycidyl methacrylate. Especially preferred acrylate adhesives are those wherein the polymeric 'backbone' includes a proportion of unreacted carboxylic acid residues, eg. acrylic acid residues. Unreacted acid residues are particularly advantageous since they may be derivatised, eg. esterified, with curable groups. Thus especially preferred acrylate copolymers are acrylate tricopolymers. A particularly preferred adhesive moiety is an alkyl acrylate/alkyl acrylate/acrylic acid tri-copolymer. An especially preferred adhesive moiety is an n-butyl acrylate/ 2-ethylhexyl acrylate/acrylic acid tri-copolymer. The most preferred tri-copolymer is n-butyl acrylate/2-ethylhexyl acrylatelacrylic acid in the ratios 47147/6. Such an adhesive composition is hereinafter referred to as A8 adhesive.

Any conventionally known unsaturated compounds, eg. olefinic or aromatic compounds, may be used as the bound-in curable moiety provided that they are able to react with the polymeric 'backbone'. Free radical curable moieties are preferred, such groups include acrylates and methacrylates which may form, for example, esters or amides with any unreacted acid groups in the polymeric 'backbone'. Curable groups which are photodimerisable may also be used and include groups such as anthracenes, cinnamates, maleimides and coumarin groups. Mixtures of all of the aforesaid may also be used. Preferred bound-in curable groups are selected from acrylates, methacrylates and anthracenes. Especially preferred bound-in curable groups are free radical curable groups such as acrylates and/or methacrylates. Most preferred are methacrylates such as hydroxyalkyl methacrylates wherein the hydroxyalkyl group possesses from 1 to 6 carbon atoms, eg. 1 to 4 carbon atoms and especially 1 or 2 carbon atoms. Especially preferred is hydroxyethylmethacrylate.

Alternatively, when the polymeric 'backbone' comprises an acrylate moiety then the bound-in curable moiety may be a free radical polymerisable vinyl moiety as hereinbefore described.

The amount of the bound-in curable moiety present in the switchable adhesive composition may vary, depending, inter alia, upon the amount of tackiness desired in the switchable adhesive when it is switched from it's tacky to it's non-tacky state. Thus, the amount of the bound-in curable moiety, eg. hydroxyethyl methacrylate, present in the switchable adhesive composition may be from 0.4 to 50% by weight of polymer backbone preferably from 0.4 to 40% by weight and more preferably from 0.4 to 20% by weight. The free radical curable moieties are preferably present as from 0.4 to 5% by weight. The photodimerisable moieties are preferably present as from 10 to 15% by weight, eg. 13% by weight.

The switchable adhesive compositions of the invention may also include a free radical initiator. Any conventionally known free radical initiators may be used. Particularly preferred are those initiators which react to visible light radiation, although initiators which react under longer or shorter wavelength light may be used in compositions of the invention. Thus, free radical initiators which may be mentioned include titanocene photoinitiators; dye/co-initiator systems, eg. thionine/triethanolamine; dye/borate salt systems; dye/peroxide systems and 1,2-diketonelco-initiator systems, eg. camphorquinone/tertiary amine. Preferred free radical initiators are the titanocene initiators such as bis($y^5$-cyclopentadienyl) bis [2,6-difluoro-3-(lH-pyrr-l-yl) phenyl]-titanium, sold as Irgacure 784 (Trade Mark) in the UK by Ciba Geigy. Initiators which react with UV light may be used, such initiators include the Irgacures. Such as Irgacure 651 (benzyl dimethyl ketal) or Irgacure 907 (2-methyl-1-[4-(methylthio)phenyl]-2-morpholino-propan-1-one); or the Uvatones, such as Uvatone 8302 (2,2-diethoxy-1,2-diphenyl ethanone).

The switchable adhesives of the invention which have a free radical bound-in curable group are preferably provided with a photoinitiator.

According to a further feature of the invention we provide a process for the manufacture of an adhesive composition as hereinbefore described which comprises reacting a polymeric 'backbone' as hereinbefore described with a curable moiety.

In particular we provide a process for the manufacture of an acrylate switchable adhesive composition as hereinbefore described which comprises reacting an unreacted carboxylic acid containing copolymer backbone with a curable, eg. photocurable, moiety to produce an adhesive composition comprising backbone polymer with bound-in curable groups as acid derivatives. The bound-in curable groups may be end groups, pendant groups or may be incorporated into the backbone.

The polyurethane adhesives of the invention may be manufactured by reacting the polyurethane with a free radical curable moiety. When the polyurethane adhesive is a linear polyurethane the bound-in curable groups may comprise any of the groups hereinbefore described, eg. acrylates or anthracenes. When the polyurethane adhesive is a cross-linked adhesive the bound-in curable group may vary depending upon the nature of the cross-linking group used in the polyurethane adhesive. For example if the polyurethane cross-linking group is a multifunctional alcohol any bound-in curable group may be used, eg. acrylates or anthracenes. Alternatively if the polyurethane cross-linking group is an acrylate or methacrylate then the bound-in curable group will preferably be a photodimerisable group, eg. anthracene. When the cross-linked polyurethane adhesive comprises an acrylate or methacrylate cross-linking group then the cross-linking group is preferably thermally initiated. Such thermally initiated compositions may also include a thermal free radical initiator.

Suitable polyurethanes for use in the switchable adhesive composition can be derived from a polyester diol or preferably a polyether diol and a di-isocyanate. Suitable polyether diols include polyoxyalkylene diols in which the alkylene contains 2 to 4 carbon atoms such as polyoxyethylene, polyoxypropylene and polyoxytetramethylene diols and mixtures thereof. Such polyether diols can suitably have an average molecular weight of 1000 to 8000 and preferably have a molecular weight of 1500 to 6000. A favoured polyether diol for forming the polyurethanes used in the invention is polyoxypropylene diol. An apt diol of this type is known as PPG 2025, available from British Drug House, which has an average molecular weight of 2025.

Another suitably hydrophilic group containing diol is a block copolymer of polypropylene glycol and ethylene oxide marketed as Dowfax 63N10 (Trade Mark) available from Dow Chemicals Inc.

Polyoxyalkylene diol residues can be used to render the adhesive formed therefrom moisture vapour transmitting.

Diisocyanates used to form the polyurethane can suitably have an isocyanate functionality of 1.6 to 2.05 and can preferably have an isocyanate functionality of 2.0. Suitable diisocyanates include a aliphatic (including alicyclic) and aromatic diisocyanates. Favoured diisocyanates include toluene diisocyanate, 4,4'-diphenylmethane diisocyanate and 4,4'-dicyclo hexyl methyl diisocyanate which is the preferred diisocyanate and which in an apt form is known as Desmodur W (Trade Mark) available from Bayer.

The polyurethane can optionally include a chain extending agent. Suitable chain extending agents include diols such as ethane diol and butane diol, diamines for example ethylene diamine, and water. The molar ratio of diol or diol and diamine residues to diisocyanate residues in the polyurethane can suitably be 0.6 to 0.8:1 and preferably 0.65 to 0.75:1 for example 0.7:1.

When an isocyanate-terminated polyurethane has been prepared it can then be reacted with one or more hydroxyl group containing compounds which react with the isocyanate groups. Preferably some of these compounds are mono-alcohols (although they may be other compounds which have a monofunctional group reacting with an isocyanate group, eg. mono-amines). One type of mono-alcohol may comprise the radiation curing group. Desirably such mono-alcohols are used to react with from 40 to 90% of the isocyanate residues of the polymer, eg. from 55 to 70%. Particularly suitable mono-ols for use with polyurethane adhesive compositions include anthracene methanol, cinnamyl alcohol and hydroxy maleimides, since these comprise groups which cure, eg. photodimerise, under the influence of UV or visible light. In some cases the dimerisation may be reversed on heating. Derivatives of such groups which are also curable may also be used. Thus the groups may be optionally substituted with substituents which do not substantially reduce curing.

Other mono-alcohols may be present in the polyurethane adhesives which comprise the cross-linking groups. Aptly, these include compounds having groups which can react with free-radicals, eg. unsaturated compounds which may be esters of acrylic or methacrylic acid in which there is at least one hydroxyl functional group which is capable of reacting with an isocyanate group.

The proportion of hydroxyl-containing compound which also contains an unsaturated functionality (if present) is desirably such as to react with from 15 to 25% of the free isocyanate groups in the polyurethane. The remainder of the free isocyanate groups can react with the other hydroxyl group containing compounds which are present as chain terminators.

In addition to the mono-alcohols discussed above, mono-ols which are tackifying agents can be used to react with free isocyanate groups of the polyurethane. Such mono-alcohols include hydrogenated mono hydroxy tackifying resins, eg. hydrogenated abietyl alcohol.

A hydrophilic polyurethane can be formed by suitable choice of polyether diol. The polyurethane when hydrated may contain from 35 to 95% by weight of water, aptly 50 to 92%, preferably 70 to 90% and more preferably 75 to 85% by weight of water. Water absorption can be obtained by taking a known weight of the polyurethane and immersing in water for 24 hours. The hydrated polymer is removed from the water, excess water is removed by lightly blotting with absorbent paper and then the hydrated polyurethane is weighed. The water absorption of the polyurethane (% by weight) can then be calculated as (weight of hydrated polyurethane-weight of dry polyurethane)×100/weight of hydrated polyurethane.

The curing reaction reacts the bound-in curable groups resulting in increased molecular weight of the adhesive polymer which may be initiated by visible light or longer or shorter wavelength light such as infra red or ultra violet light. Whilst it is preferable that the bound-in curable moiety reacts via a free radical reaction, it is most desirable that the reaction of the curable groups is visible light initiated. Thus the wavelength of the light used may be less than 700nm, eg. preferably between 400 and 700nm.

The dosage of light used may vary depending upon the switchable adhesive composition but is generally greater than 0.4 mW cm$^{-2}$ when UV light is used. When a visible light switchable adhesive is used ambient light may be used and therefore the dosage may vary.

The adhesive compositions of the invention may also be blended with a conventional adhesive composition to produce an adhesive mixture which is itself switchable. It is a further feature of the present invention to provide a switchable adhesive as hereinbefore described in admixture with an adhesive composition.

By the term adhesive composition we mean a composition comprising conventional adhesives known per se, such conventional adhesives are non-switchable adhesives.

Thus according to the invention we provide a switchable adhesive composition comprising an adhesive polymeric moiety and a visible light curable moiety.

The adhesives of the invention are preferably pressure sensitive adhesives (PSAs) and are particularly advantageous in the manufacture of adhesive tapes and adhesive dressings. By the term dressings we include wound dressings, adhesive bandages and adhesive tapes for medical use. The adhesives may also be useful in the manufacture of other conventional products which require a peelable adhesive, eg. masking tapes, stencils, etc.

Thus according to the invention we provide the use of a composition as hereinbefore described in the manufacture of an adhesive dressing.

Dressings comprising adhesive compositions of the invention are also themselves novel.

Thus according to a further feature of the invention we provide an adhesive dressing comprising a backing layer substantially coated on at least one surface thereof with an adhesive as hereinbefore described.

The adhesive coating may be a continuous coating on non-continuous, eg. may be a pattern spread adhesive.

The backing layer preferably comprises a light occlusive layer and a transparent or translucent layer. By the term light occlusive we particularly mean that the material is occlusive over the wavelength range that the photoinitiator absorbs in. Thus we especially prefer a light occlusive layer which is visible light occlusive. The light occlusive and transparent layers may be laminated together or alternatively the light occlusive layer may have a low peel strength adhesive on it's transparent layer facing surface.

Thus in use an adhesive dressing of the invention may be applied to the skin of a patient. When it is desired to remove or replace the dressing the light occlusive layer may be removed. The adhesive on the skin facing surface of the transparent layer can then be exposed to either visible light or a light source and after a given time the peel strength of the adhesive will be reduced allowing the transparent layer to be removed from the patient's skin.

Thus according to the invention we provide a dressing as hereinbefore described comprising a backing layer and an adhesive layer, wherein the backing layer comprises a removable light occlusive layer and a transparent layer intermediate the occlusive layer and the adhesive layer and wherein the adhesive layer comprises a switchable adhesive as hereinbefore described.

Any conventionally known occlusive and transparent materials may be used in the backing layer of the dressings of the invention. Preferred dressings are those which comprise a film, ie. thin film, backing layer, ie. both the occlusive and transparent layers comprise a film, although other backing layers, eg. fabric layers, may also be considered appropriate.

The dressings of the invention may be manufactured using conventional methods known oer se.

The occlusive layer of the backing layer may be adhesively bonded to the transparent layer or may be laminated thereto. If adhesively bonded then the peel strength of the bonding adhesive must be less than that of the switchable adhesive in its tacky form.

The dressings of the invention are especially useful in the treatment of wounds. Thus according to a further feature of the invention we provide a method of treating a wound on a patient which comprises applying a dressing as hereinbefore described to the wound of a patient. The method may also include the removal of the dressing by removing the light occlusive layer of the dressing and then irradiating the adhesive through the transparent or translucent layer to render the adhesive non-tacky.

Many medicinal agents may be incorporated into the adhesive compositions of the present invention. By medicinal agent is meant pharmacologically active agents including agents which are topical anaesthetics such as xylocaine, bacteriostatic agents such as silver nitrate; anti-bacterial agents of which preferred forms are silver sulphadiazine and chlorhexidine salts; antibiotics; topical steroids, enzymes; tissue stimulants; coagulants and anticoagulants and anti-fungal agents. Other agents such as emollients may also be added.

The invention will now be illustrated with reference to the accompanying drawings and Examples.

Figure 1:
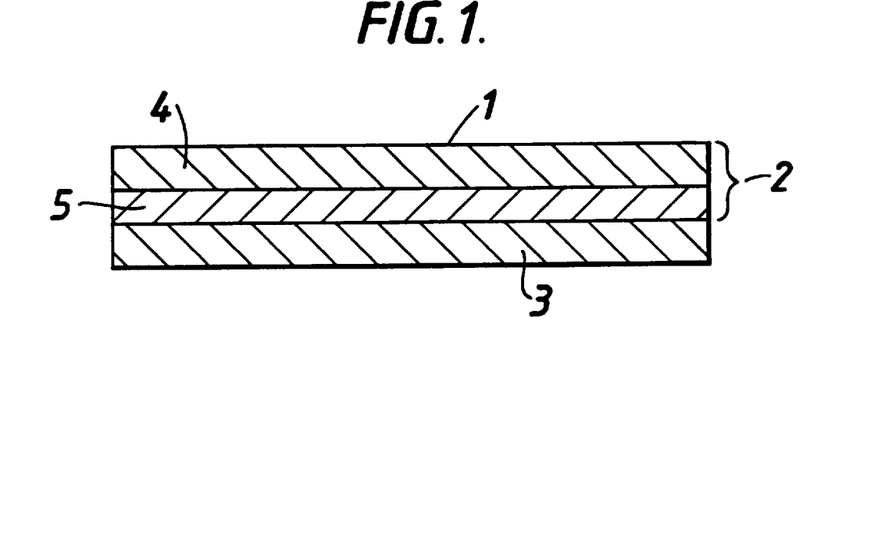
FIG. 1 is a cross-section of a dressing of the invention.

With reference to FIG. 1, a dressing (1) comprises a backing layer (2) and an adhesive layer (3). The backing layer (2) comprises an occlusive layer (4) and a transparent layer (5) intermediate the occlusive layer (4) and the adhesive layer (3). The dressing may optionally be provided with appropriate carrier layers and protector layers.

In use the dressing (1) is adhered to the skin of a patient when the adhesive layer (3) is in a tacky form. When it is desired to remove the dressing (1) from the patient, the occlusive layer (4) is removed exposing the transparent layer (5) and thereby the adhesive layer (3) to visible light. The visible light causes the photoinitiator to initiate the free-radical cross-linking of the PSA through the pendant acrylate groups resulting in the adhesive losing its tackiness and peel strength. The time required for this reaction to be complete may vary, eg. from 1 to 15 minutes. The dressing may then be removed with reduced trauma to the patient.

Figure 2:
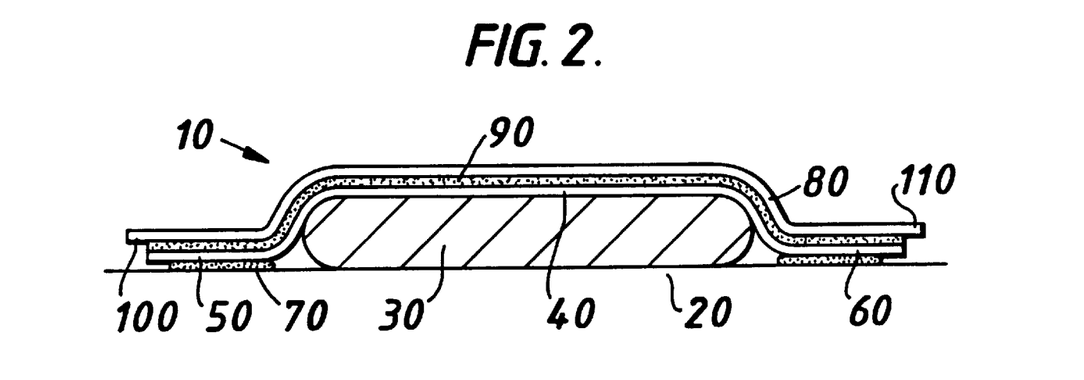
FIG. 2 is a cross-section of a further dressing embodiment of the invention.

The present invention will now be described by way of example only, with reference to the accompanying drawing, wherein FIG. 2 illustrates schematically in cross-section a medical dressing according to the present invention when in use on patient.

Referring now to FIG. 2, a medical dressing (10) is shown attached to a patient's skin (20). The dressing (10) comprises a wound facing absorbent layer (30) which is underneath a protective backing layer (40) at opposed edges (50, 60) the backing layer (40) is provided with adhesive (70) comprises groups which can be cross-linked under the influence of UV or visible light.

The backing layer (40) is provided with a cover (80) which is releasably secured to the backing layer (40) by a weak adhesive (90). Alternatively the cover (80) may be laminated to the backing layer (40). For ease of removal the cover (80) overlaps the backing layer (40) at its edges (100, 110).

When it is desired to remove the dressing from the skin of a patient, the cover (80) can be gripped at its edges (100, 110) and peeled off the backing layer (40) so as to expose the adhesive (70) to UV or visible light irradiation. This irradiation acts so as to cure the adhesive which, after a certain time (depending upon the adhesive used), causes the adhesive (70) to lose its tackiness to such an extent so that the dressing can be removed without causing trauma to the patient.

In order that the removal of the cover (80) does not itself cause trauma to the patient, the peel strength of the adhesive (90) adhering the cover (80) to the backing layer (40) should be substantially less than that of the adhesive (70) adhering the dressing (10) to the patient's skin.

Since the adhesive (70) loses tackiness on exposure to UV or visible light, it is desirable that the adhesive (70) is not exposed to the light for a substantial period when the dressing (10) is applied to a patient. Thus the adhesive (70) may be initially provided on the surface with release paper (not shown) which is opaque to UV and visible light and which can be readily removed from the adhesive so that the dressing is ready for use.

The preparation and testing of adhesives suitable for use as the adhesive layer (70) will now be described in the following Examples.

The following Trade Marks are referred to herein:

| Trade Mark | Chemical/Apparatus | Company |
|---|---|---|
| Desmodur W | 4,4-Dicyclohexylmethane diisocyanate | Bayer UK Ltd |
| Metatin 812ES | Dioctyltin dilaurate | Acima Chemical Industries Ltd Inc |
| Abitol | Hydroabietyl Alcohol | Hercules Inc |
| Melinex | Grade 542 polyethyleneterephthalate | ICI Films |
| AIBN | -Azo-iso-butyronitrile | Fisons |
| Irgacure 651 | Benzildimethyl ketal | Ciba-Geigy |
| Irgacure 784 | Bis($y^5$-cyclopentadienyl) bis[2,6-difluoro-3-(1,4-pyrr-1-yl) phenyl]-titanium | Ciba-Geigy |
| Michler's Ketone | 4,4'-Bis(dimethylamino)- benzophenone | Aldrich |
| Uvahand 250 | UV Lamp | Dr Honle |

EXAMPLE 1

Preparation of Acrylate/HEMA Switchable Adhesive

Weight of A8 Adhesive solution=97.02 g (32% solids) (equivalent to 0.0259 mols of acrylic acid).

Weight of 1,1'-Carbonyldiimidazole=4.19 g (0.0259 mols)

Weight of 1,8-Diazabicyclo[5,4,0]undec-7-ene (DBU)= 3.93 g (0.0259 mols)

Weight of Hydroxyethyl Methacrylate (HEMA)=3.36 g (0.0259 mols)

A stirred solution of A8 adhesive in acetone was bubbled through with nitrogen for approx 30 minutes before the carbonyidiimidazole was added. The nitrogen bleed was then removed and a bubbler was attached to the round-bottom flask to monitor the production of carbon dioxide. This was left for approx 3 hours at 45° C. The HEMA and DBU were added to the adhesive solution at 45° C. and left to stir for 3 hours. The sample was then left to stand for two days at room temperature to give a pale orange solution. The esterified solution was then added to diethyl ether and washed with 80 ml of a 10% aqueous hydrochloric acid solution. After separation the switchable adhesive solution was washed with 80 ml water and left to separate. The switchable adhesive solution was washed with 80 ml of a 10% aqueous potassium hydrogen carbonate solution and left to separate. The separated diethyl ether solution of switchable adhesive was dried over anhydrous sodium sulphate and then filtered.

EXAMPLE 2

Preoarations of Switchable PSAs with Iraecure 784 Photoinitiator

Samples of Acrylate/HEMA switchable adhesives were prepared by mixing Irgacure 784 photoinitiator with the product of Example 1.

a) Adhesive of Example 1=42.1318 g
   Weight of solid=5.9406 g
   Weight of Irgacure 784=0.5741–0.0020=0.572 g=9.61% b) Adhesive of Example 1*=40.6247 g
   Weight of solid=4.9968 g
   Weight of Irgacure 784=0.5020 g=10.0%

*Adhesive prepared as in Example 1, washed in dichloromethane rather than diethyl ether.

Adhesive solution 'a' was spread with a 0.030 inch spreading block onto Melinex and dried in a darkened fume cupboard. Peel strength testing was carried out from HDPE film and irradiation from a halogen lamp. The adhesive solution 'b' was spread with a 0.024 inch spreading block.

The two adhesive spreads were irradiated under a halogen lamp for switching for the peel strength studies. Irradiation time was 15 mins.

EXAMPLE 3

Peel Strength Tests

The formulation of Example 2a) contained 9.6% Irgacure 784 and that of 2b) contained 10% Irgacure 784 photoinitiator. Samples were spread at about 30 $gm^{-2}$ onto Melinex film. The samples were spread in an enclosed fume cupboard (darkened) and kept in a blacked out environment.

Adhesion to HDPE film, was based on the test described in the British Pharmacoepia (1988), Appendix XX, method H—adhesives test 2., except that: Peeling was after 30 minutes. The specimens were cut and laminated to the HDPE film coated steel plates in the dark, under a red safelight and either were kept in the dark until peeling or were exposed to a halogen type light for half of the 30 minute dwell, after 10 minutes build up, (and allowed to cool for the last 5 minutes). Samples were transported and kept in light proof boxes until actual peeling.

Peel strength results are shown in Table I.

TABLE I

| | Peel Strength ($Nm^{-1}$) from HDPE Film | | |
|---|---|---|---|
| Example | Irgacure Content | Unirradiated | After Light Radiation |
| 2a) | 9.6% | 32 | 6 |
| 2b) | 10% | 63 | 6 |

EXAMPLE 4

Preparation of Polyurethane Adhesives 1.32 g of polyethylene glycol (PEG) 600 was placed in an oven at 90° C. for 15 mins to aid handling. 23.319 of polypropylene glycol (PPG) 2025, the melted PEG 600, 0.37 g of ethanediol (EDO) and 13.32 g of Desmodur W were added to a 250 ml flange flask. The flask was placed in a water bath at 90° C. and the contents stirred to achieve a homogeneous mixture. This having been achieved, 0.1 g of Metatin 812ES was added and 50 ml of carbon tetrachloride was added as a solvent. The mixture was stirred for a further hour at 90° C. to give a prepolymer composition. Meanwhile, 4.64 g of Abitol was placed in the oven at 60° C. for 15 mins, 0.01 g 4-methoxyphenol was dissolved in 0.58 g of 2-hydroxyethyl methacrylate and 6.47 g of 9-anthracene methanol was mobilised with 30 ml carbon tetrachloride.

The 2-HEMA solution was then added to the prepolymer composition, followed by the 9-anthracene methanol washed through with further amounts of carbon tetrachloride (~10 ml) and stirring was then continued for a further 30 mins.

The Abitol was then added and the reaction mixture stirred in a water bath (90°) for 30 mins.

The resultant switchable adhesive solution was then left overnight to cool and was found to be a golden liquid of apparently low viscosity (approximately 20% solids content).

EXAMPLE 5

Preparation of Films

The solution of Example 4 was used to produce four films.

a) Film 5a)

14.70 g of the solution of Example 4 (corresponding to 3.0 g of solids) was mixed with 1% w/w relative to the solids content of the solution, of AIBN and of Irgacure 651. Thus 0.039 of AIBN and of Irgacure 651 were added to the switchable adhesive solution and were stirred until well mixed.

The solution was then spread to a depth of 0.010 inches thickness on Melinex and left to dry overnight at room temperature in the dark.

The dried 5a) film was thermally cured in an oven at 80° C. for 4 minutes. The film was laminated to release paper by applying light finger pressure and stored in a dark cupboard for further use. Lamination was to the embossed side of the polyethylene sheet. The laminate was then cut into strips. The strips were then placed for varying periods under a Uvahand R50 UV irradiation source, ranging from 0–10 mins. The UV source was a 230 watt UV lamp which was used with a filter so that it emitted UV light of a wavelength above 300nm. In the experiments detailed herein this lamp was held at a distance of approximately 1 foot from a sample to be irradiated. Exposure was through the Melinex layer, ie. this layer was held facing the lamp.

Thermal curing alone produced an adhesive with a reasonable peel strength. Low UV irradiation (for 1 or 2 minutes) did not have any apparent effect on the properties of the adhesive (peel strength was assessed approximately by manually peeling the polyethylene sheet off the adhesive and noting how difficult it was to do this). Tackiness was assessed approximately by inserting a blunt object in the adhesive, rapidly withdrawing it and noting the tendency of the adhesive to prevent withdrawal of the object. However after 5 minutes irradiation a decrease in both peel strength and tackiness was apparent.

Irradiation for 10 mins produced a very noticeable shrinkage of the adhesive (apparent after exposure of more than 5 mins irradiation), resulting in slight curving and twisting of the laminated film. The adhesive itself peeled very easily and cleanly.

A film exposed for 2 mins to the UV light was removed from the polyethylene and irradiated for a further 2 mins so the adhesive was exposed to UV without it having passed through Melinex. This resulted in a large reduction in tack and also in peel strength. Cure times were approximately halved when the PSA was irradiated directly in this manner rather than through the Melinex.

b) Film 5b)

The same procedure was used as preparing the film 5a), except that Irgacure 784 (a visible light initiator) was used rather than Irgacure 651 (a UV initiator).

To 17.28 g of the solution of Example 4, 0.0353 g of AIBN and 0.0353 g of Irgacure 784 were added and, after mixing, the liquid was spread to a depth of 0.010 inches on Melinex and left to dry at room temperature overnight in the dark.

c) Film 5c)

The same procedure was used as for preparing the film 5a) except that only thermal initiator (AIBN) was used.

To 17.33 g of the solution of Example 4, 0.0355 g of AIBN was added and, after mixing the liquid was spread to a depth of 0.010 inches on Melinex and left to dry at room temperature overnight in the dark.

A small sample of film 5c) was left on Melinex exposed to the light in a laboratory (some fluorescent light and some natural light through windows) over approximately 60 hours and this was found to have resulted in complete loss of tack.

A separate sample of film 5c) was thermally cured at 80° C. for 15 mins and monitored when left at room temperature exposed to the light in a laboratory (fluorescent lighting as well as natural light coming through windows). The results obtained are summarised below in Table II:

TABLE II

| Exposure Time | Properties of Adhesive |
|---|---|
| 00 mins | good adhesive, good tack |
| 03 mins | good adhesive, less tack |
| 05 mins | poorer adhesive, much less tack |
| 10 mins | poor adhesive, little tack |
| 15 mins | poor adhesive, little tack |
| 20 mins | poor adhesive, little tack |
| 25 mins | poor adhesive, little tack |
| 30 mins | poor adhesive, little tack |
| 35 mins | poor adhesive, little tack |

Complete loss of tack was not achieved after 24hrs, although tackiness was very low after this period.

A sample of film 5b) and film 5c) was left in a UV cabinet for 10 mins. After this irradiation time it was found that film 5b) cured more completely than film 5c).

d) Film 5d)

The same procedure was used as for film 5a) except that a photosensitiser was used instead of a photoinitiator. This was done in order to avoid the influence of free radicals produced by photoinitiation since it was believed that such free radicals were not necessary for detackification of the adhesive to occur. The photosensitiser used was Michler's Ketone.

To 37.26 g of the solution of Example 4, 0.0758 g of AIBN was added, as well as 0.0550 g of Michler's Ketone. After mixing, a 0.010 inches film was spread on Melinex and left overnight at room temperature.

EXAMPLE 6

Peel Tests of Films 5a) and 5d)

a) Film 5a)

Strips of film 5a) having a width of 25 mm were applied to a polyethylene film of the type described above which has been first laminated to a steel plate to keep it flat. Light finger pressure, followed by two passes of a 2 kg roller (width 1¾", diameter 4") was used to laminate the film 5a) strips to the polyethylene film, with the adhesive layer contacting the polyethylene film at its embossed surface (which mimics the surface of skin).

The strips were allowed to remain laminated to the polyethylene film for 20 mins at 23° C. in a 50% relative humidity environment and were then peeled off the polyethylene at a rate of 300 mm/min along the length of the strips and using a 180° C. peel as test described in British Pharmacopoeia Appendix XXH (Test 2). Some of the film 5a) samples laminated to the polyethylene were exposed to UV light for 15 mins of the said 20 mins (wavelength greater than 300 mm, frequency 50 Hz) whereas others were left in the dark the whole time.

The results are illustrated in Table III:

TABLE III

| Sample | Peel Strength (N/m) without UV light | Peel Strength (N/m) with UV light |
|---|---|---|
| 1 | 313 ) | 33.5) |
| 2 | 309.5) Average: 309 | 24 ) Average: 33 |
| 3 | 204.5) | 38.5) |

An average reduction in peel strength of 89% was thus obtained using UV curing.

b) Film 5d)

The procedure given for 5a above was repeated using film 5d) instead and the results obtained are illustrated in Table IV:

TABLE IV

| Sample | Peel Strength (N/m) without UV light | Peel Strength (N/m) with UV light |
|---|---|---|
| 1 | 357.5) | 35 ) |
| 2 | 350.5) Average: 314.5 | 30.5) Average: 31.5 |
| 3 | 355.5 | 29 ) |

An average reduction in peel strength of 91% was thus obtained using UV curing, which is approximately the same as for film 5a).

EXAMPLE 7

Preparation of Polyurethane-anthracene Adhesives

Polyurethane-anthracene switchable adhesives were prepared using the method of Example 4. The results are illustrated in Table V:

EXAMPLE 8

Peel Strength Tests

Peel strength tests were carried out using the method of Example 2. The adhesives were peeled from a number of different substrates, steel, high density polyethylene (HDPE) and pig skin. Once laminated to the substrate the adhesives were either kept in the dark or irradiated under a UV source for a set time, always ensuring the same dwell time for both sets of adhesives. Changes in peel strength were therefore monitored by comparing the irradiated samples to the unirradiated control samples. The results are illustrated in Table VI:

TABLE VI

| Sample No. | Substrate | Method of Film Preparation | Average Peel Strength (no UV cure) $Nm^{-1}$ | Average Peel Strength (UV cured) $Nm^{-1}$ | Irradiation time minutes |
|---|---|---|---|---|---|
| 7a i) | HDPE | Ex 5a) | 618 | 66 | 15 |
| 7a ii) | HDPE | Ex 5d) | 729 | 63 | 20 |
| 7b | HDPE | Ex 5d) | 277 | 55 | 30 |
| 7c i) | HDPE | Ex 5c) | 593 | 55 | 30 |
| 7c ii) | HDPE | Ex 5d) | 579 | 28 | 30 |
| 7c iii) | Pig Skin | Ex 5d) | 103 | 58 | 15 |

EXAMPLE 9

Preparation of Acrylate-anthracene Adhesives

Acrylate adhesives were prepared as for Example 1 with the monomer mix as 6 g acrylic acid, 47 g butyl acrylate and 47 g ethyl hexyl acrylate.

The adhesive was converted to a switchable adhesive. The method used for esterification of the carboxylic acid groups pendant to the prepolymer chain employed a dehydrating agent, dicyclohexylcarbodiimide (DCC). This was used in conjunction with a dimethylaminopyridine catalyst with the reaction proceeding at room temperature. The following general procedure was initially used for the esterification reaction. For Example 9a), 6.09 g of base PSA (containing 0.0068 moles acrylic acid) was placed in a dry jar along with 1.41 g of anthracenemethanol (0.0068 moles), 1.39 g DCC (0.0068 moles) and 0.33 g DMAP (0.00027 moles). Approximately 100 ml of anhydrous tetrahydrofuran (THF) was added to the reaction mixture which was left stirring overnight (~24 hours). A precipitate was formed as a by-product of the esterification (dicyclohexylurea, DHU) which was insoluble in THF and was therefore filtered from the PSA solution. A viscous yellow liquid was produced which was then spread thinly onto Melinex for UV irradiation.

Further conversions were made and the results are shown in Table VII:

TABLE V

| Sample No. | PPG2025 Eqvs OH | PEG600 Eqvs OH | Ethanediol Eqvs OH | Glycerol Eqvs OH | NCO:OH | 2-HEMA Eqvs OH | Abitol Eqvs OH | Anthracene Methanol Eqvs OH |
|---|---|---|---|---|---|---|---|---|
| 7a) | 1.7 | 0.3 | 0.8 | — | 2.18 | 0.3 | 0.9 | 2.09 |
| 7b) | 1.7 | — | 0.8 | 0.25 | 2.20 | 0.3 | 0.9 | 2.09 |
| 7c) | 1.7 | 0.3 | 0.8 | — | 2.28 | 0.8 | 0.9 | 2.09 |

TABLE VII

| Sample | No Moles of Acrylic Acid (in polymer) | No Moles of Anthracene Methanol | No Moles of DCC | No Moles of DMAP | Target AM Incorporation | Comments |
|---|---|---|---|---|---|---|
| 9a) | 0.0068 (6.09 g polymer) | 0.0068 (1.41 g) | 0.0068 (1.39 g) | 0.0027 (0.33 g) | 8% | Reaction at room temp for 24 hrs in 100 ml THF |
| 9b) | 0.0062 (5.58 g) | 0.0031 (0.64 g) | 0.0031 (0.63 g) | 0.0012 (0.15 g) | 4% | Reaction at room temp for 24 hrs in 100 ml THF |
| 9c) | 0.0048 (4.32 g) | 0.0011 (0.23 g) | 0.0011 (0.23 g) | $4.1 \times 10^{-4}$ (0.05 g) | 2% | Repeat of 9c), reaction at room temp for 24 hrs in 80 ml THF |

The anthracene methanol (AM) incorporation is illustrated in Table VIII:

TABLE VIII

| Sample | Target AM Incorporation | Actual AM Incorporation |
|---|---|---|
| 9a) | 8% | 1.95% |
| 9b) | 4% | 2.44% |
| 9c) | 2% | 1.14% |

The favoured approach for the esterification reaction was to react any excess acrylic acid (remaining from the reaction with anthracenemethanol) with methanol, this being added after the anthracenemethanol had reacted.

The switching results are illustrated in Table IX:

TABLE IX

| Sample | % Incorporated AM in PSA | Irridiation Time | Result |
|---|---|---|---|
| 9a) | 1.95 | 12 mins | low-tackfilm |
| 9a) | 1.95 | 20 mins | non-tacky film |
| 9a) | 1.95 | 45 mins | hard, non-tacky film |
| 9b) | 2.44 | 30 mins | non-tacky film |
| 9c) | 1.14 | 30 mins | low-tack film |
| 9c) | 1.14 | 1 hr | non-tacky film |

EXAMPLE 10

Preparation of Acrylate Switchable Adhesives

Acrylate adhesives were prepared using ethyl hexylacrylate (EHA), butyl acrylate (BA) and acrylic acid (a) were prepared using the method of Example 1.

The switchable adhesives were mixed with Irgacure photoinitiator. Samples were spread onto Melinex film. The samples were spread in an enclosed fume cupboard (darkened) and kept in a blacked out environment.

Adhesion to HDPE film, was based on the test described in the British Pharmacoepia (1988), Appendix XX, method H—adhesives test 2., except that: Peeling was after 30 minutes. The specimens were cut and laminated to the HDPE film coated steel plates in the dark, under a red safelight and either were kept in the dark until peeling or were exposed to light. Samples were transported and kept in light proof boxes until actual peeling.

The results are illustrated in the following Tables in which peel strength tests were carried out using:

halogen lamp (Table XI)

ambient light (Table X)

UV light (Table XI)

TABLE IX

Reductions in peel strength when irradiated with halogen lamp (1 foot from sample):

| Esterified PSA | % EHA | % BA | % AA | % HEMA Incorp. | % Irgacure 784 | Irradiation time (mins) | Mass Weight (gsm) | Peel Strength No Irradn. (N/m) | Peel Strength Irradiated (N/m) |
|---|---|---|---|---|---|---|---|---|---|
| 10a) | 44 | 44 | 7.27 | 4.73 | 10 | 15 | 34 | 180 | 13 |
|  |  |  |  |  | 10 | 2 | 34 | 180 | 21 |
|  |  |  |  |  | 10 | 15 | 23 | 140 | 10 |
|  |  |  |  |  | 10 | 5 | 23 | 140 | 15 |
|  |  |  |  |  | 10 | 2 | 23 | 140 | 20 |
| 10b) | 45 | 45 | 5.83 | 4.17 | 10 | 15 | 38 | 300 | 25 |
|  |  |  |  |  |  | 2 | 38 | 300 | 47 |
|  |  |  |  |  | 10 | 15 | 37 | 300 | 20 |
|  |  |  |  |  |  | 5 | 37 | 300 | 25 |
|  |  |  |  |  |  | 2 | 37 | 300 | 50 |
| 10c) | 47 | 47 | 2.92 | 3.08 | 10 | 15 | 32 | 348 | 53 |
|  |  |  |  |  | 10 | 15 | 39 | 280 | 35 |
|  |  |  |  |  |  | 5 | 39 | 280 | 45 |
|  |  |  |  |  |  | 2 | 39 | 280 | 60 |
|  |  |  |  |  |  | 1 | 39 | 280 | 120 |
|  |  |  |  |  | 5 | 15 | 30 | 277 | 55 |
|  |  |  |  |  |  | 5 | 30 | 277 | 63 |
|  |  |  |  |  |  | 2 | 30 | 277 | 77 |
|  |  |  |  |  | 2 | 15 | 28 | 265 | 59 |
|  |  |  |  |  |  | 5 | 28 | 265 | 102 |
|  |  |  |  |  |  | 2 | 28 | 265 | 110 |

TABLE IX-continued

Reductions in peel strength when irradiated with halogen lamp (1 foot from sample):

| Esterified PSA | % EHA | % BA | % AA | % HEMA Incorp. | % Irgacure 784 | Irradiation time (mins) | Mass Weight (gsm) | Peel Strength No Irradn. (N/m) | Peel Strength Irradiated (N/m) |
|---|---|---|---|---|---|---|---|---|---|
| 10d) | 46 | 46 | 7.16 | 0.84 | 10 | 15 | 30 | 140 | 19 |
| | | | | | 10 | 5 | 30 | 200 | 30 |
| | | | | | | 2 | 30 | 200 | 32 |
| | | | | | 5 | 15 | 28 | 120 | 23 |
| | | | | | 5 | 15 | 32 | 200 | 33 |
| | | | | | | 5 | 32 | 200 | 47 |
| | | | | | | 2 | 32 | 200 | 75 |
| | | | | | 2 | 15 | 31 | 190 | 51 |
| | | | | | | 5 | 31 | 190 | 84 |
| | | | | | | 2 | 31 | 190 | 140 |
| 10e) | 45 | 45 | 4.31 | 5.69 | 10 | 15 | 36 | 300 | 19 |
| | | | | | 5 | 15 | 39 | 337 | 22 |
| | | | | | 5 | 15 | 40 | 260 | 30 |
| | | | | | | 5 | 40 | 260 | 30 |
| | | | | | | 2 | 40 | 290 | 30 |
| | | | | | | 15 | 38 | 290 | 20 |
| | | | | | | 5 | 38 | 290 | 25 |
| | | | | | | 2 | 38 | 290 | 25 |
| 10f) | 44 | 44 | 7.18 | 4.82 | 10 | 15 | 23 | 80 | 15 |
| | | | | | | 5 | 23 | 80 | 12 |
| | | | | | | 2 | 23 | 80 | 12 |
| | | | | | 5 | 15 | 22 | 91 | 15 |
| | | | | | | 5 | 22 | 91 | 12 |
| | | | | | | 2 | 22 | 91 | 15 |
| | | | | | 2 | 15 | 22 | 84 | 15 |
| | | | | | | 5 | 22 | 84 | 15 |
| | | | | | | 2 | 22 | 84 | 14 |
| 10g) | 47 | 47 | 3.0 | 3.0 | 10 | 15 | 27 | 100 | 15 |
| | | | | | | 5 | 27 | 100 | 20 |
| | | | | | | 2 | 27 | 100 | 20 |
| | | | | | 5 | 15 | 21 | 85 | 20 |
| | | | | | | 5 | 21 | 85 | 20 |
| | | | | | | 2 | 21 | 85 | 20 |
| | | | | | 2 | 15 | 21 | 80 | 25 |
| | | | | | | 5 | 21 | 80 | 25 |
| | | | | | | 2 | 21 | 80 | 25 |
| 10h) | 45 | 45 | 6.62 | 3.38 | 5 | 15 | 20 | 130 | 30 |
| | | | | | | 5 | 20 | 130 | 30 |
| | | | | | | 2 | 20 | 130 | 40 |
| | | | | | | 1 | 20 | 130 | 45 |
| | | | | | 2 | 15 | 34 | 200 | 40 |
| | | | | | | 5 | 34 | 200 | 60 |
| | | | | | | 2 | 34 | 200 | 90 |
| 10i) | 46 | 46 | 4.92 | 3.08 | 10 | 15 | 26 | 65 | 15 |
| | | | | | | 5 | 26 | 65 | 15 |
| | | | | | | 2 | 26 | 65 | 20 |
| | | | | | | 1 | 26 | 65 | 25 |
| | | | | | 5 | 15 | 26 | 65 | 15 |
| | | | | | | 5 | 26 | 65 | 15 |
| | | | | | | 2 | 26 | 65 | 20 |
| | | | | | | 1 | 26 | 65 | 30 |
| | | | | | 2 | 15 | 26 | 100 | 20 |
| | | | | | | 5 | 26 | 100 | 20 |
| | | | | | | 2 | 26 | 100 | 20 |
| | | | | | | 1 | 26 | 100 | 30 |
| 10j) | 46 | 46 | 5.03 | 2.97 | 5 | 15 | 26 | 120 | 20 |
| | | | | | | 5 | 26 | 120 | 25 |
| | | | | | | 2 | 26 | 120 | 30 |
| | | | | | | 1 | 26 | 120 | 55 |
| | | | | | 2 | 15 | 25 | 110 | 30 |
| | | | | | | 5 | 25 | 110 | 35 |
| | | | | | | 2 | 25 | 110 | 45 |
| | | | | | | 1 | 25 | 110 | 55 |

TABLE X

Reductions in peel strength when irradiated with ambient light

| Esterified PSA | % EHA | % BA | % AA | % HEMA Incorp. | % Irgacure 784 | Irradiation time (mins) | Mass Weight (gsm) | Peel Strength No Irradn. (N/m) | Peel Strength Irradiated (N/m) |
|---|---|---|---|---|---|---|---|---|---|
| 10k) | 46 | 46 | 7.16 | 0.84 | 10 | 15 | 30 | 140 | 28 |
| | | | | | | 30 | 30 | 140 | 17 |
| | | | | | | 120 | 30 | 140 | 13 |
| | | | | | 5 | 15 | 28 | 120 | 28 |
| | | | | | | 30 | 28 | 120 | 30 |
| | | | | | | 120 | 28 | 120 | 21 |
| 10l) | 45 | 45 | 4.31 | 5.69 | 10 | 15 | 36 | 300 | 72 |
| | | | | | | 30 | 36 | 300 | 31 |
| | | | | | | 120 | 36 | 300 | 16 |
| | | | | | 5 | 15 | 39 | 337 | 52 |
| | | | | | | 30 | 39 | 337 | 38 |
| | | | | | | 120 | 39 | 337 | 22 |

TABLE XI

Reductions in peel strength when irradiated with low dose UV

| Esterified PSA | % EHA | % BA | % AA | % HEMA Incorp. | % Irgacure 784 | Irradiation time (mins) | Mass Weight (gsm) | Peel Strength No Irradn. (N/m) | Peel Strength Irradiated (N/m) |
|---|---|---|---|---|---|---|---|---|---|
| 10m) | 46 | 46 | 4.92 | 308 | 1 | 5 | | 140 | 30 |
| | | | | | 1 | 5 | | 150 | 20 |
| 10n) | 46 | 46 | 5.03 | 2.97 | 1 | 2 | 20 | 115 | 80 |
| | | | | | 2 | 2 | 20 | 140 | 40 |
| | | | | | 3 | 2 | 26 | 160 | 30 |

EXAMPLE 12

Acrylic PSA cross-lnked with acrylate 111 g toluene was refluxed at 70° C. under nitrogen for 20 mins. To this was added 0.0718 of bis(4-t-butylcyclohexyl)-peroxy carbonate initiator (BCHPC) and then a monomer mixture of 46 g ethyl hexyl acrylate, 46 g butyl acrylate, 8 g itaconic anhydride was added over 1.5 hours to the reaction vessel. A further 30 g toluene was added to the reaction after the monomer addition and then left for 1.5 hours. A solution of 0.4482 g BCHPC in 40 ml toluene was then added to the reaction in 10 ml aliquots every 30 mins. The reaction was then left stirring under nitrogen for 4 hours after a further 126 g toluene had been added. Note 1% by weight of Irganox 1010 may be added to the PSA if required. The PSA produced above was then reacted with 2-hydroxyethyl methacrylate (equimolar quantity with regard to itaconic anhydride) in the presence of catalytic quantity of sulphuric acid at ~50° C. This reaction was complete in 10 hours to give a PSA with pendant methacrylate groups. This reaction can also be carried out with HEMA and itaconic anhydride interchanged.

The switchable PSA was blended with 2% and 5% Irgacure 784 by weight and spread onto Melinex at 39 gm$^{-2}$ and 50 gm$^{-2}$ respectively. Once dried the PSA was peeled from HDPE film both before and after 15 mins irradiation from a visible light lamp.

The results are illustrated in Table XII:

TABLE XII

| Irgacure 784 | Peel Strength before irradiation | Peel Strength after irradiation |
|---|---|---|
| 2% | 208 Nm$^{-1}$ | 46 Nm$^{-1}$ |
| 5% | 287 Nm$^{-1}$ | 14 Nm$^{-1}$ |

EXAMPLE 13

The reaction was carried out as for Example 12 except that itaconic anhydride was replaced with 3-isopropenyl-α, α-imethyl benzyl isocyanate (m-TMI) in a solvent selected from toluene, acetone or ethyl acetate.

The base PSA was converted to a switchable PSA by reacting the base PSA containing m-TMI with 2-hydroxyl ethyl methacrylate (equimolar quantity with regard to m-TMI) in the presence of 1% (by wt of m-TMI) of dibutyl tin dilaurate catalyst. This reaction was carried out at 50° C. for 8 hours.

The switchable adhesive was spread as for Example 12 with 2 and 5% Irgacure 784 by wt of switchable adhesive. The results are illustrated in Table XI:

TABLE XIII

| Irgacure 784 | Peel strength before | Peel strength after 15 mins visible light |
|---|---|---|

| Content % | Spread gm$^{-2}$ | irradiation Nm$^{-1}$ | irradiation Nm$^{-1}$ |
|---|---|---|---|
| 5 | 31 | 255 | 23 |
| 2 | 30 | 208 | 28 |

What is claimed is:

1. A switchable adhesive composition, having an adhesion which decreases on irradiation with visible light, said adhesive composition comprising an adhesive polymer, an adhesive polymeric moiety and a plurality of bound in visible light curable groups chemically bound to the adhesive polymeric moiety the curing reaction of said curable moieties being initiatable by visible light.

2. A switchable adhesive composition according to claim 1 wherein the adhesive polymeric moiety comprises an acrylate adhesive.

3. A switchable adhesive composition according to claim 2 wherein the acrylate adhesive is an acrylate copolymer.

4. A switchable adhesive composition according to claim 3 wherein the acrylate copolymer is an alkyl acrylatelalkyl acrylate/acrylic acid tri-copolymer.

5. A switchable adhesive composition according to claim 4 wherein the acrylate copolymer is an n-butyl acrylate/2-ethylhexyl acrylate/acrylic acid tri-copolymer.

6. A switchable adhesive composition according to claim 1 wherein the bound-in curable groups are selected from acrylates, methacrylates and anthracenes.

7. A switchable adhesive according to claim 1 wherein the bound-in curable groups are free radical curable groups.

8. A switchable adhesive composition according to claim 1 wherein the adhesive polymeric group comprises a polymeric backbone and wherein the amount present of bound-in curable groups is from 0.4 to 50% by weight of polymer backbone.

9. A switchable adhesive composition according to claim 1 which includes a photoinitiator.

10. A process for the manufacture of a switchable adhesive composition according to claim 1 which comprises reacting an adhesive polymeric moiety with a curable moiety.

11. An adhesive medical dressing comprising a backing layer substantially coated on at least one surface thereof with a switchable adhesive composition comprising an adhesive polymeric moiety and a plurality of bound-in curable groups.

12. An adhesive medical dressing according to claim 11 wherein the backing layer comprises a light occlusive layer and a transparent or translucent layer.

13. An adhesive medical dressing comprising a backing layer and an adhesive layer wherein the backing layer comprises a removable light occlusive layer and a transparent or translucent layer intermediate the adhesive layer and the light occlusive layer and wherein the adhesive layer comprises an adhesive composition according to claim 1.

14. A switchable adhesive composition comprising an adhesive polymeric moiety and a plurality of bound-in visible light curable groups, the adhesive polymeric moiety comprising an acrylate adhesive, the acrylate adhesive comprising an alkyl acrylate/alkyl acrylate/acrylic acid tri-copolymer.

15. A switchable adhesive composition according to claim 14, wherein the acrylate adhesive comprises n-butyl acrylate/2-ethylhexyl acrylate/acrylic acid tri-copolymer.

* * * * *